United States Patent [19]

Genshaw et al.

[11] 4,211,845

[45] Jul. 8, 1980

[54] GLUCOSE INDICATOR AND METHOD

[75] Inventors: Marvin A. Genshaw; William I. White, both of Elkhart, Ind.

[73] Assignee: Miles Laboratories, Inc., Elkhart, Ind.

[21] Appl. No.: 963,332

[22] Filed: Nov. 24, 1978

[51] Int. Cl.² .................................... G01N 33/16
[52] U.S. Cl. ............................ 435/14; 23/230 B; 252/408; 422/56; 435/25; 435/28
[58] Field of Search .............. 23/230 B; 195/103.5 R, 195/103.5 C; 252/408; 422/56; 435/14, 25, 28

[56] References Cited

U.S. PATENT DOCUMENTS

| | | | |
|---|---|---|---|
| 3,123,443 | 3/1964 | Smeby | 23/230 B X |
| 3,164,534 | 1/1965 | Free | 23/230 B X |
| 3,233,974 | 2/1966 | Bradley | 23/230 B X |
| 3,290,228 | 12/1966 | Gretton et al. | 23/230 B X |
| 3,298,789 | 1/1967 | Mast | 23/230 B X |

OTHER PUBLICATIONS

Holland et al., "A Safer Substitute for Benzidine in the Detection of Blood", Tetrahedron, vol. 30, No. 18, Sep. 1974, pp. 3299–3302.

Primary Examiner—Arnold Turk
Attorney, Agent, or Firm—Roger N. Coe

[57] ABSTRACT

Glucose indicator, test means and method for assaying glucose in fluids are disclosed. More specifically, a new indicator formulation comprising an enzyme system which includes a substance having glucose oxidase activity, a substance having peroxidative activity and a mixture of syringaldazine and 3,3',5,5'-tetramethylbenzidine are disclosed for indicating the presence of glucose in industrial and body fluids. The indicator formulation is nonmutagenic and can be used in conjunction with instrumentation designed to quantitatively measure whole blood glucose levels within the range of 10 to 400 milligrams (mg) per 100 milliliters (ml).

14 Claims, 1 Drawing Figure

GLUCOSE INDICATOR AND METHOD

FIELD OF THE INVENTION

The invention relates to diagnostic indicators for indicating the presence of glucose in fluids and, more particularly, to an indicator system for the detection and estimation of glucose in industrial and body fluids. The invention is especially applicable to the determination of the presence and amount of glucose in urine and blood as an aid to the physician in his diagnosis and treatment of diabetes.

BACKGROUND OF THE INVENTION

The determination of glucose in body fluids, such as urine or blood, is of importance not only in the case of diabetic patients who must control their sugar input, but it is also important in those situations in which the detection of disease as a public health measure requires the screening of the urine or blood of large numbers of people. Because early diagnosis and continued control are so important in diabetes, a glucose test, to be of greatest value to the physician in his diagnosis and control of the disease, must be conveniently rapid, simple enough to serve the clinician and sensitive enough to reflect meaningful variations in urine or blood glucose.

A number of methods exist for measuring or estimating the amount of reducing sugars in body fluids. Some older methods were based on the use of alkaline copper solutions which were heated with the material being tested to precipitate cuprous oxide. These older methods have the disadvantage that their use requires a certain amount of skill and familiarity with the use of measuring equipment and in general do not meet the desiderata of simplicity, accuracy and economy.

Diagnostic tablet procedures, as described in U.S. Pat. No. 2,387,244, found wide usage because of the fact that such procedures could be executed by unskilled persons and the procedures provided an inexpensive, quick, convenient method for the daily testing of urine. While the use of a diagnostic tablet was superior to older techniques, heat was still necessary to perform a test and this meant that a certain degree of care had to be exercised in the compounding and subsequent handling of compositions to eliminate the possibility of unintentional generation of heat by accidental wetting of the diagnostic tablet.

With the development of reagent strips having impregnated areas containing a reagent system including glucose oxidase, peroxidase and a chromogen indicator system, a significant and important breakthrough for achieving a simple, rapid and convenient method for the detection and estimation of the presence of glucose in fluids was achieved. As described, for example, in U.S. Pat. Nos. 2,981,606; 3,092,465; 3,164,534 and 3,298,789 semiquantitative measurement of blood glucose is achieved using reagent strips having a test system based on the enzymatic reaction of glucose oxidase. The use of such test strips provides the user with immediate estimation of the glucose content of a blood sample, and when used in conjunction with a reflectance colorimeter, quantitative results are obtainable which are fully comparable with older and more difficult laboratory procedures.

There are indications, however, that certain of the chromogen indicators which have been used in the past in such reagent strips may be tumorigenic or mutagenic. Among the suspected compounds are such materials as o-tolidine, benzidine, and 2,7-diamino fluorene, all of which have been used as chromogen indicators for indicating the presence of glucose in fluids. Indicator systems have been sought which are safer to use than some of the older indicators and which are at least equally effective.

SUMMARY OF THE INVENTION

An object of the present invention is to provide an improved glucose indicator system and means for detecting the presence of glucose.

Another object of the present invention is to provide an improved glucose indicator which will distinguish between glucose and other reducing substances and detect small amounts of glucose in a fluid, particularly in an aqueous liquid.

Still another object of the present invention is to provide inexpensive, quick and convenient means for determining the presence and amount of glucose in a fluid.

Yet another object of the present invention is to provide a glucose indicator capable of determining glucose in a test sample within a time period ranging from about 30 to about 120 seconds.

A further object of the present invention is to provide a nonmutagenic indicator system for indicating the presence of glucose in fluids.

In accordance with the present invention a glucose indicator comprising an enzyme system having glucose oxidase activity, a substance having peroxidative activity and, as a color-forming substance oxidizable by hydrogen peroxide in the presence of said substance having peroxidative activity, a mixture of syringaldazine and 3,3',5,5'-tetramethylbenzidine. The molar ratio of the 3,3',5,5' tetramethylbenzidine to syringaldazine can range from about 1:8 to about 8:1, with a preferred ratio of these indicators being from about 2:6 to about 1:1 and an especially preferred ratio being 3:5, respectively. 3,3',5,5'-tetramethylbenzidine is nontumorigenic and nonmutagenic. Syringaldazine is not structurally related to any known carcinogen or mutagen. Advantageously, the combination of 3,3',5,5'-tetramethylbenzidine and syringaldazine results in a glucose indicator capable of being used in conjunction with instrumentation designed to quantitatively measure whole blood glucose values within the range of 10 to 400 milligrams per 100 milliliters.

BRIEF DESCRIPTION OF THE DRAWINGS

Other and further objects, advantages and features of the invention will be apparent to those skilled in the art in the following detailed description thereof, taken in conjunction with the accompaning drawing in which.

DESCRIPTION OF THE PREFERRED EMBODIMENTS

Figure 1:
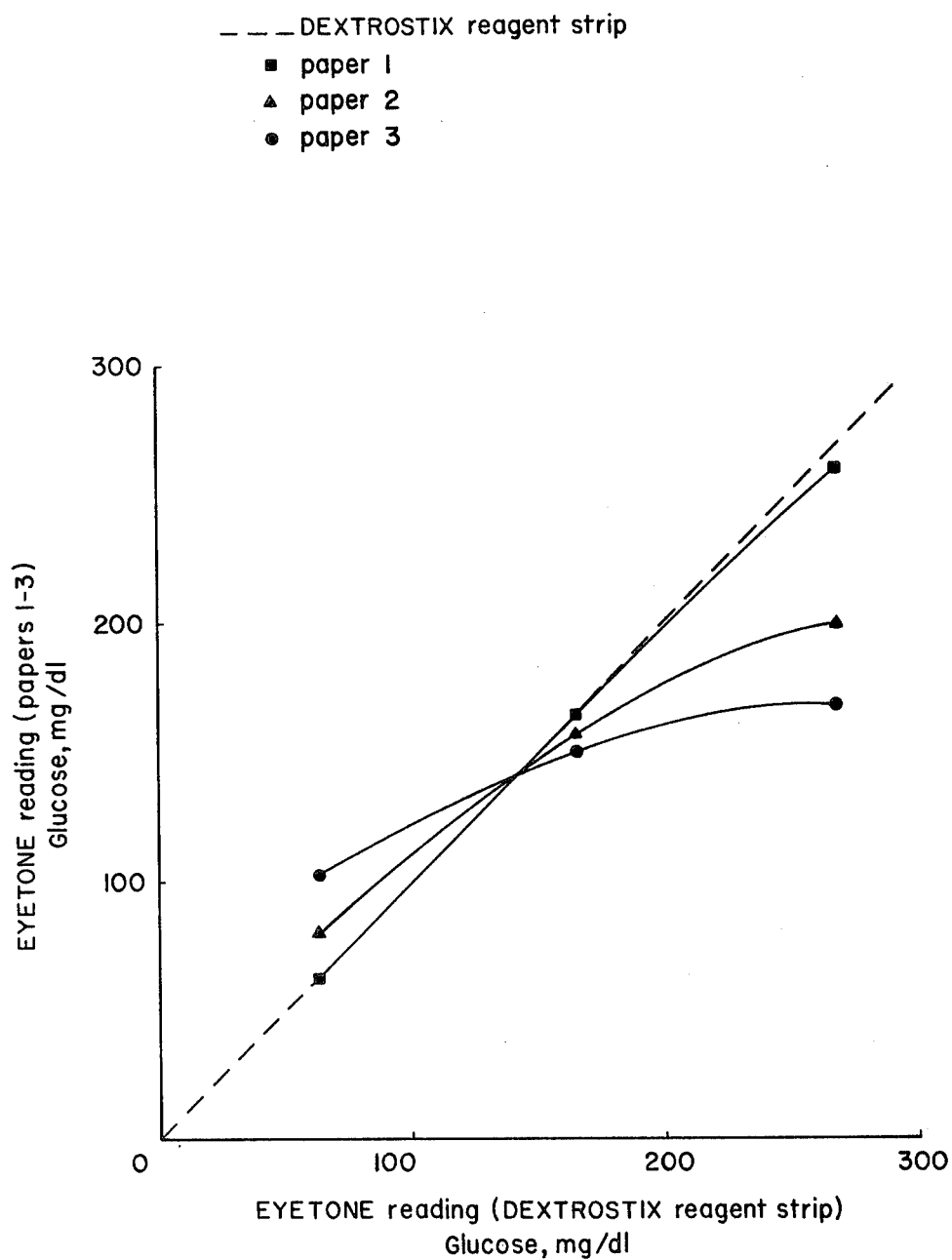
FIG. 1 is a graph showing the correlation between three reagent strips (prepared in accordance with Example II) and DEXTROSTIX ® reagent strip (Ames Company, Elkhart, Indiana).

For the purpose of this application the term "fluids" shall be understood to refer to body fluids, such as blood serum, blood plasma, urine, spinal fluids and, in addition, shall refer to aqueous solutions containing urea. Although the most preferred application of the test means and process of this invention is to body fluids, such as blood and urine, it should be understood that the disclosed test means and process can be applied to industrial fluids as well.

The invention contemplates in its broader aspects an indicator system comprising an enzyme system having glucose oxidase activity and a substance capable of undergoing a color change with one or more of the compounds formed during the action of the enzyme upon compounds formed upon reaction with glucose containing fluids. In a test, glucose present in a fluid sample converts to gluconic acid. Hydrogen, removed from the glucose by the glucose oxidase, combines with atmospheric oxygen to form hydrogen peroxide. In the presence of the peroxidase, hydrogen peroxide oxidizes the indicators producing a detectable color.

Glucose enzymes which can be used are those which will react with a glucose-containing fluid being tested to produce a predetermined reaction product, such as hydrogen peroxide. For example, glucose oxidase obtained from molds can be used. These are usually referred to as the flavo-protein type since they contain as a prosthetic group or coenzyme a flavin or isoalloxazine.

Preferably, a dual enzyme system is present: one enzyme transforms glucose to produce hydrogen peroxide, whereas the other enzyme has peroxidative activity. Substances having peroxidative activity which are useful in the present invention can be chosen from various organic and inorganic sources. Plant peroxidases, such as horseradish peroxidase or potato peroxidase, can be used. Inorganic compounds having peroxidase activity include iodides, such as sodium and ammonium iodides, and molybdates, such as potassium and ammonium molybdates. In addition, urohemin and a number of other porphyrin substances having peroxidative activity can be used. Other substances which are not enzymes, but which have peroxidative activity include such compounds as iron sulfocyanate, iron tannate, ferrous ferrocyanide, potassium chromic sulfate and the like.

The color-forming mixture of the present invention reactable with peroxidase and peroxidase-like substances to produce a color formation in the presence of hydrogen peroxide is a mixture of 3,3',5,5'-tetramethylbenzidine and syringaldazine in a molar ratio of from about 1:8 to about 8:1, with a preferred ratio of these color-forming indicators being between about 2:6 to about 1:1 and a particularly preferred ratio being 3:5, respectively. The color-forming mixture enables a color spectrum to be obtained which ranges from light green, representing about 25 mg glucose per 100 ml blood, for example, through medium-purple, representing about 100 mg glucose per 100 ml of blood, to dark purple, representing about 400 mg glucose per 100 ml of blood. Conveniently, a spectrum is obtained having distinct color shades for different levels of glucose. While the individual indicators have been known to be useful in tests for glucose, their specific combination provides a substantial advance in the technology of obtaining sharp reproducible readings at given glucose levels and provides a color range which is readable by commerically available colorimetric equipment.

Since the compositions employed to measure glucose in blood, for example, should be maintained at a pH level in the range of about pH 4 to pH 7.5, a buffer system comprising tris (hydroxymethyl) amino methane, malonic acid and disodium malonate is particularly useful for this purpose.

An interpolymer of methylvinyl ether and maleic anhydride is also useful in the formulation of glucose indicators of the present invention. One such interpolymer is marketed commercially under the trademark Gantrez-AN by GAF Corporation. When this interpolymer is dissolved in an alcohol it forms a partial ester derivative, and when the interpolymer is dissolved in water it forms an acid derivative. Since test means prepared in accordance with the present invention are typically prepared from aqueous alcohol solutions test compositions in the final product will contain either an acid derivative or a partial ester derivative or a mixture of said derivatives. The presence of the above described interpolymer derivatives along with polyvinyl pyrrolidone having, for example, an average molecular weight of about 40,000, greatly enhance the color formed when color forming indicators are oxidized by hydrogen peroxide in the presence of peroxidase. This enhancement of color aids in more sharply defining different color shades for different levels of glucose content in a given fluid sample. This is particularly important to the physician in diagnosing the presence of an incipient diabetic condition.

The glucose indicator of the invention can be in the form of a treated paper, a bottled reagent, a frangible capsule containing the indicator in reagent form, a pill or tablet which can be dropped into water or alcohol or the fluid being tested for glucose, or a solid alcohol gel containing the reagent. When in pill or tablet form the indicator may contain a heat-generating substance, such as lithium chloride, which provides heat when placed in water, thus accelerating the reaction rate.

The preferred glucose indicator is prepared by treating a suitable carrier matrix with glucose indicator composition in the form of liquid reagent. The expression "carrier matrix" refers to either bibulous or nonbibulous matrices which are insoluble in and maintain their structural integrity when exposed to water or other physiological fluids. Suitable bibulous matrices which can be used include paper, cellulose, wood, synthetic resin fleeces, woven and nonwoven fabrics and the like. Nonbibulous matrices include glass fiber and organoplastic materials, such as polypropylene and the like. The carrier matrix can be soaked, immersed in, sprayed or printed with the liquid reagent and the carrier matrix thereafter dried by suitable means, such as ambient or forced air drying. The matrix can advantageously be affixed to an insoluble support member such as an organoplastic strip, e.g., polystyrene, by suitable means, such as double faced adhesive tape, for ease of use.

When the test composition is to be used for detecting glucose in blood, the surface of the impregnated carrier matrix is normally covered with a semipermeable transparent coating film of ethyl cellulose or other suitable material. This can be accomplished by applying a layer of ethyl cellulose dissolved in benzene, for example, to the surface of the impregnated carrier matrix and then removing the solvent by evaporative drying.

Glucose indicators in the form of treated carrier matrices are often stored for considerable periods of time before use, and it is therefore desirable that the reagents chosen are not easily auto-oxidizable in air. Advisably, the carrier matrix should be protected from exposure to light and in some cases it is desirable to keep the carrier matrix sealed in a moisture repellent package which is opened only shortly before use. The reagent ingredients can also be chosen to provide different degrees of sensitivity. For example, by the proper choice of reagents, different colors can be produced to indicate different concentrations of glucose, rather than one color of varying color intensity.

If desirable, a carrier matrix can be treated with a background dye of a particular color, such as yellow, so that the color produced by the test reaction is blended with the background color to produce varying tints which correspond to the concentration of glucose present in the fluid or liquid being tested. It may be especially desirable to dye the matrix yellow when the test color produced is blue.

For highly precise determinations of glucose concentration photoelectric colorimetric or spectrophotometric methods can be employed to determine color indication. The EYETONE ® reflectance colorimeter (Ames Company, Division of Miles Laboratories, Inc.) is a portable instrument designed to quantitatively measure whole blood glucose when used in conjunction with DEXTROSTIX ® reagent strips (Ames Company, Division of Miles Laboratories, Inc.). The EYETONE reflectance colorimeter measures the reflective light from the surface of the reagent area of such reagent strips and converts this measurement, by means of electronic circuitry, to a reading on a precisely calibrated meter scale on the instrument capable of indicating blood glucose within the range of 10 to 400 mg/100 ml. The higher the blood glucose level, the darker the strip and the less light reflected. Conversely, the lower the blood glucose level the lighter the strip and the more light reflected. The color-forming mixture described herein has been found to be especially useful in that it provides an unique color response which can be determined by the EYETONE reflectance colorimeter in a fashion similar to that of DEXTROSTIX reagent strips. Alternatively, semiquantitative results can be obtained using the glucose indicator of the present invention by comparing the color produced with a panel of standard colors obtained with known concentrations of glucose employing the same glucose indicator.

While, as previously indicated, the glucose indicator of the present invention can be employed to detect the presence or quantity of glucose in a biological fluid, such as urine and blood, the indicator is equally applicable to the detection and determination of glucose in nonbiological fluids, such as liquids produced during the manufacture of beer, dried eggs, beverage syrups and the like.

In order to more clearly disclose the nature of the present invention, specific examples illustrating the practice of the invention will hereinafter be described. It should be understood, however, that this is done solely by way of example and is intended neither to delineate the scope of the invention nor limit the ambit of the appended claims.

EXAMPLE I

Filter paper (Eaton and Dikeman No. 204) was impregnated with the following solution:

| Material | Amount |
| --- | --- |
| distilled water | 40 ml |
| ethanol | 40 ml |
| 5% solution of Gantrez AN-139 (stabilizer from GAF Corporation, New York, N.Y.) | 52 ml |
| tris-malonate buffer (2.8 molar tris amine; 1.4 molar malonic acid; 1.4 molar malonate) | 32 ml |
| polyvinyl pyrrolidone (10% in water) | 28 ml |
| peroxidase in 4.3 ml glucose oxidase (1000 units per ml) and 19.3 ml distilled water | 200 mg |

The impregnated filter paper was then dried at 60° C. Following drying the filter paper was impregnated with a solution comprising 1.5% ethylcellulose (weight per volume) in a four-to-one chloroform-methanol mixture containing 7.5 millimolar 3,3',5,5'-tetramethylbenzidine and 12.5 millimolar syringaldazine. The thus impregnated paper was dried at 50° C. and cut into strips which were mounted on polystyrene backing using double-faced adhesive tape.

Blood specimens of known glucose content were tested using the strips thus prepared, and an EYETONE ® reflectance colorimeter was used to read the resulting colors. Prior to use, the EYETONE reflectance colorimeter was calibrated with neutral density calibration chips and a glucose calibrator. The low and high readings of the EYETONE reflectance colorimeter were adjusted at 50 and 400 mg/dl with two neutral density calibration chips. The calibration of the instrument was checked by reacting a strip with a standard glucose solution (130 mg/dl) for one minute and reading it on the EYETONE reflectance colorimeter. Deviations were adjusted by a control knob to read 130 mg/dl.

In reading the strips the following procedure was used. Whole blood was deposited on the strip with an eye-dropper and allowed to react for 60 seconds. At the end of the period, the strip was washed with water, blotted dry and read immediately on the calibrated EYETONE reflectance colorimeter. When a plot was made of the known glucose values versus values determined with the strip of this example, a straight line was obtained with a slope of 0.94, an intercept of −7.9, an R=0.99 and an average standard deviation of 7.4.

When tests identical to Example I were run using dimethylamino antipyrine, aminoantipyrine or napthalene indigo as the color-forming material insufficient color production was obtained.

EXAMPLE II

Three different paper formulations were prepared from the following basic formula:

A first impregnating solution was prepared from the following three solutions. Solution a contained 0.4 g of the sodium salt of syringaldazine added to 35 ml hot water to which was added 3 g polyvinylpyrrolidone. Solution b contained 0.1 g tetramethylbenzidine, 8 ml hot water, 25 ml ethanol, 12 ml 10% (w/v) Gantrez AN-139 and 20 ml 1.5 M citrate buffer, pH 4.8. Solution c contained 0.8 ml glucose oxidase ($5.0 \times 10^3$ IU/ml) and 123 mg horseradish peroxidase (90.8 IU/mg). Solution b was added to solution a and solution c was added to the mixture. The final pH of the resulting impregnating solution was 5.0 which resulted in the formation of a syringaldazine suspension therein.

A second impregnating solution was 1.75% (w/v) ethyl cellulose in chloroform.

Impregnated paper was prepared by saturating E & D 204 paper (Easton and Dikeman) with the first impregnating solution and drying at 80° C. for 15 minutes in a forced-air oven. The paper was then saturated a second time with the non-aqueous second impregnating solution and dried at 40° C. for 10 minutes. The impregnated paper was applied to plastic support members or handles in such a manner that a matrix 0.2"×0.4" was located at one end of each support member.

The three different paper formulations were prepared as follows:

Paper 1 was prepared as described.

Paper 2 was prepared as described, except that the solution b used contained no tetramethyl benzidine.

Paper 3 was prepared as described, except that the solution a used contained no syringaldazine.

Blood specimens of known glucose content were tested using strips made from the impregnated papers thus produced, and the resulting colors were read using an EYETONE ® reflectance colorimeter. Prior to use, the EYETONE was calibrated with neural density chips and a glucose calibrator. The low and high readings of the EYETONE reflectance colorimeter were adjusted at 50 and 400 mg/dl with two neutral density chips. The calibration of the instrument was checked by reading a DEXTROSTIX ® strip with a standard glucose solution (130 mg/dl) for one minute and reading it on the EYETONE reflectance colorimeter. Deviations were adjusted by a control knob to read 130 mg/dl.

In reading the strips the following procedure was used. Whole blood was deposited on the strip with an eyedropper and allowed to react for 60 seconds. At the end of this period, the strip was washed with water, blotted dry and read on the calibrated EYETONE reflectance colorimeter twenty seconds after the wash. These strips were compared in performance with the product DEXTROSTIX reagent strips, which was treated in the same manner, except that the reading was made immediately after the wash, as described in the product instructions.

Strips made with papers 1, 2 and 3, as well as the DEXTROSTIX reagent strip standards, were tested with spiked whole blood solutions of glucose at levels of 62 mg/dl, 130 mg/dl, 165 md/dl, and 270 mg/dl and the results are shown in FIG. 1. As will be noted, the formula containing the mixture of tetramethylbenzidine and syringaldazine has a good correlation with the current DEXTROSTIX reagent strips and EYETONE reflectance colorimeter, while the individual indicators alone gave unsatisfactory correlations.

EXAMPLE III

Filter paper (Eaton and Dikeman 204) was impregnated with the following solution:

| | |
|---|---|
| Distilled water | 20 ml |
| Ethanol | 20 ml |
| 5% solution of Gantrez AN-139 | 26 ml |
| Tris-Malonate buffer (2.8 M tris amine; 1.4 M malonate) | 16 ml |
| Polyvinylpyrrolidone (10% in water) | 14 ml |
| Horseradish peroxidase in 1.5 ml glucose oxidase (1221 U/ml) in 9.7 ml distilled water. | 100 mg |

The impregnated filter paper was then dried at 60° C. Following drying, the filter paper was impregnated with a solution comprising 1.5% ethyl cellulose (W/V) in a four-to-one chloroform-methanol mixture containing 7.5 millimolar tetramethylbenzidine and 12.5 millimolar syringaldazine.

The impregnated paper was dried at 50° C. and cut into strips which were then mounted on polystyrene backing using double-faced adhesive tape.

Color chips were chosen to correspond to blood glucose levels of 25, 45, 90, 130, 175 and 250 mg/dl. Solutions of glucose in blood were prepared at glucose levels of 25, 45, 90, 130, 175, 250 and 350 mg/dl. Two persons were asked to read the strips by depositing blood on the strip with an eyedropper, allowing it to react for one minute, washing with water, blotting and comparing the color to the chips. (Solutions were identified to readers only by letters). Results were as follows:

| Solution (Glucose concentration in mg/dl) | | |
|---|---|---|
| | Reader 1 | Reader 2 |
| A(90) | 130 | 130 |
| B(250) | 250 | 250 |
| C(45) | 45 | 45 |
| D(130) | 130 | 130 |
| E(90) | 130 | 130 |
| F(25) | 25 | 25 |
| G(90) | 90 | 90 |
| H(350) | 250 | 250 |
| I(25) | 25 | 25 |
| J(130) | 175 | 130 |
| K(175) | 130 | 175 |

Although agreement is not perfect, use of the strip to detect glucose levels in blood in a qualitative manner is possible, in conjunction with the color chips.

From the foregoing, it will be seen that this invention is well adapted to attain all of the ends and objects hereinabove set forth, together with other advantages which are obvious and which are inherent to the system. It will be appreciated that the invention provides an improved method of and means for detecting glucose. The disclosed glucose indicator system is simple, inexpensive, quick and convenient.

It will be evident that various additives can be incorporated into the reagent composition. Such additives include suitable protective agents, thickening agents, wetting agents, suspending agents and the like, as well as inert dyes to impart a uniform color background. Instead of an ethyl cellulose coating, other coating compositions such as cellophane, cellulose acetate, cellulose butyrate, cellulose nitrate, cellulose acetate propionate and the like can be usd to form a semi-permeable coating or film.

Obviously, many other modifications and variations of the invention as hereinbefore set forth can be made without departing from the spirit and scope thereof.

What is claimed is:

1. A glucose indicator comprising glucose oxidase, a substance having peroxidase activity and a color-forming substance oxidizable by hydrogen peroxide in the presence of said peroxidase, said color-forming substance consisting of a mixture of 3,3',5,5',-tetramethylbenzidine and syringaldazine.

2. The glucose indicator of claim 1 in which the 3,3',5,5'-tetramethylbenzidine and syringaldazine are present in a molar ratio ranging from about 1:8 to about 8:1, respectively.

3. The glucose indicator of claim 1 in which the 3,3'5,5'-tetramethylbenzidine and syringaldazine are present in a molar ratio of from about 2:6 to about 1:1, respectively.

4. The glucose indicator of claim 1 in which the 3,3',5,5'-tetramethylbenzidine and syringaldazine are present in a molar ratio of 3:5, respectively.

5. Method for determining the presence of glucose in a fluid sample, which method comprises bringing a sample to be tested into contact with the glucose indicator as defined in claim 1 and observing any color change.

6. Method for determining the presence of glucose in a fluid sample, which method comprises bringing a sample to be tested into contact with the glucose indicator as defined in claim 2 and observing any color change.

7. Method for determining the presence of glucose in a fluid sample, which method comprises bringing a sample to be tested into contact with the glucose indicator as defined in claim 3 and observing any color change.

8. Method for determining the presence of glucose in a fluid sample, which method comprises bringing a sample to be tested into contact with the glucose indicator as defined in claim 4 and observing any color change.

9. The test means comprising a carrier matrix incorporating the glucose indicator of claim 1.

10. Test means comprising a carrier matrix incorporating the glucose indicator of claim 2.

11. Test means for detecting glucose in a fluid which comprises a bibulous material incorporating a mixture which consists essentially of an enzyme system which includes a substance having glucose oxidase activity, a substance having peroxidative activity, polyvinyl pyrrolidone, a derivative of an interpolymer of methylvinyl ether and maleic anhydride, a buffer system consisting essentially of a tris (Hydroxymethyl)-amine methane, malonic acid and disodium malonate and an indicator mixture which is oxidized in the presence of a peroxide and the substance having peroxidative activity and which changes color thereon, said indicator mixture consisting essentially of a mixture of 3,3',5,5'-tetramethylbenzidine and syringaldazine in a molar ratio from about 1:8 to 8:1, respectively.

12. Test means as described in claim 11 in which the test means also has a semi-permeable coating of a transparent ethylcellulose film over the impregnated bibulous material.

13. A method for determining the presence of glucose in a fluid sample comprising contacting a sample to be tested with the test means of claim 9 and observing any color change.

14. A method for determining the presence of glucose in a fluid sample comprising contacting a sample to be tested with the test means of claim 10 and observing any color change.

* * * * *